(12) United States Patent
Antal et al.

(10) Patent No.: US 6,743,505 B2
(45) Date of Patent: Jun. 1, 2004

(54) BIOABSORBABLE MULTIFILAMENT YARN AND METHODS OF MANUFACTURE

(75) Inventors: Attila Antal, Trenton, NJ (US); Gaoyuan Chen, Hillsborough, NJ (US); Dominick Egidio, Flanders, NJ (US); Anthony Tiano, Whiting, NJ (US); Edward Walker, Stockton, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 10/205,926

(22) Filed: Jul. 26, 2002

(65) Prior Publication Data

US 2003/0219596 A1 Nov. 27, 2003

Related U.S. Application Data

(60) Provisional application No. 60/308,264, filed on Jul. 27, 2001.

(51) Int. Cl.$^7$ .............................. D02G 3/00; D01D 5/12
(52) U.S. Cl. ................. 428/364; 428/394; 264/210.8; 264/210.7; 264/211.17; 264/235.6; 606/230; 606/231
(58) Field of Search ................. 528/271; 264/210.8, 264/210.5, 210.7, 211.17, 235.6; 428/364, 394; 606/230, 231

(56) References Cited

U.S. PATENT DOCUMENTS

| | | | | |
|---|---|---|---|---|
| 649,898 A | * | 5/1900 | Berry | 406/103 |
| 3,636,956 A | * | 1/1972 | Schneider | 606/224 |
| 5,451,461 A | * | 9/1995 | Broyer | 428/364 |
| 6,005,019 A | * | 12/1999 | Liu | 523/105 |
| 6,419,866 B1 | * | 7/2002 | Karl et al. | 264/148 |
| 2002/0077448 A1 | * | 6/2002 | Antal et al. | 528/271 |
| 2002/0125595 A1 | * | 9/2002 | Tunc | 264/40.1 |
| 2002/0180096 A1 | * | 12/2002 | Karl et al. | 264/148 |

* cited by examiner

Primary Examiner—Cynthia H. Kelly
Assistant Examiner—J. M. Gray

(57) ABSTRACT

The present invention relates to a process of forming bioabsorbable, multifilament yarn from Lactide-rich copolymers, including the steps of extruding and spinning a Lactide-rich copolymer to form a spun multifilament yarn, pre-tensioning the spun multifilament yarn to form a pre-tensioned yarn, heating the pre-tensioned yarn to form a pre-tensioned, preheated yarn, annealing and drawing the pre-tensioned, preheated yarn for a first time, annealing and drawing the yarn for a second time, cooling the twice-drawn yarn to a lower temperature, and taking-up the cooled multifilament yarn, to yarns prepared by the process and to medical devices prepared from such yarns.

10 Claims, 1 Drawing Sheet

BIOABSORBABLE MULTIFILAMENT YARN AND METHODS OF MANUFACTURE

This application claims the benefit of a provisional Application No. 60/308,264 filed Jul. 27, 2001.

BACKGROUND OF THE INVENTION

There are difficulties in producing high tenacity multifilament yarns from long-term biodegradable copolymers of lactide/glycolide containing a majority of lactide. For example, in attempts to prepare multifilament yarns from such copolymers, it was found that excessive broken ends were generated in certain processes. In addition, the speed at which such a multifilament yarn is fed through the process had to be lowered to as low as 15 m/min in order to obtain acceptable process conditions and yarn properties.

U.S. Pat. No. 5,288,516 discloses a method to make high tenacity yarn with low incidence of filament breakage from a polyglycolic acid polymer at relatively high production speed. In this case, a lubricant was applied to the multifilament bundle, which then was drawn in 2 stages around a heated draw pin. However, this method cannot be applied to the Lactide rich copolymer because the melt-spun filaments made from such copolymers typically are too brittle to be drawn around a draw pin.

U.S. Pat. No. 5,232,648 and 5,425,984 disclose a low-shear extrusion process for making bioabsorbable yarns from a polymer containing 70–85% lactide. However, the resulting melt-spun filaments could be drawn only to a draw ratio of about 1.5× to about 2.7×. In addition, maximum fiber tenacity achieved was 5.0–6.7 g/d, while the elongation was as low as about 14%. Such low elongation in the fiber can readily lead to excessive filament breakage and operational difficulties in the downstream processing, such as twisting and braiding the filaments together to make suture or other surgical articles.

U.S. Pat. No. 5,688,451 teaches the use of jet entanglement to imbed broken filaments in order to improve the downstream process. However, the broken filaments still are present in the product and typically are detected at the final inspection, causing rejection of product and reduced yield.

U.S. Pat. Nos. 5,585056 and 6,005,019 recommend plasticizers as process aids to improve yarn drawability and yarn properties. Although relatively high tenacity is achieved, the elongation at break of the suture made from a polymer, even with high percentage of flexible chains, e.g. 92.5:7.5 molar ratio poly(glycolide-co-lactide), still dropped to less than 20%.

It would be advantageous to provide a process for making long-term bioabsorbable, biocompatible multifilament yarn from Lactide rich copolymers for use in the fabrication of medical devices, e.g. sutures, surgical mesh, etc., which process produces improved yield of multifilament yarn at higher speeds, and which produces multifilament yarns of relatively high tenacity, elongation and work-to-rupture.

SUMMARY OF THE INVENTION

The present invention relates to a process of forming long-term bioabsorbable, biocompatible multifilament yarn from Lactide-rich copolymers, comprising the steps of extruding a copolymer comprising from about 80% to about 98% Lactide to form a multifilament spun yarn, applying a tension of at least about 5 grams to the spun multifilament yarn to form a pre-tensioned yarn, heating the pre-tensioned yarn at a temperature of from about 60° C. to about 99° C. for a period of not more than about 6 seconds to form a pre-tensioned, preheated yarn, annealing and drawing the pre-tensioned, preheated yarn for a first time by about 4× to about 6× at a temperature of from about 110°C. to about 150° C. and for a time of from about 0.1 to about 2 seconds, annealing and drawing the yarn for a second time by about 1.05× to about 1.3× at a temperature of from about 60° C. to about 150° C. and for a time of from about 0.1 to about 2 seconds, preferably from about 0.3 to about 0.9 seconds, cooling the twice-drawn yarn to a lower temperature, and taking the multifilament yarn up. The process provides a long-term bioabsorbable, biocompatible multifilament yarn comprising from about 80% to about 98% Lactide having a tenacity of at least about 6 g/d, an elongation of at least about 26%, and work-to-rupture of at least about 20 g-cm/d. Surgical sutures also are provided which are manufactured from such multifilament yarn.

DETAILED DESCRIPTION OF THE INVENTION

Figure 1:
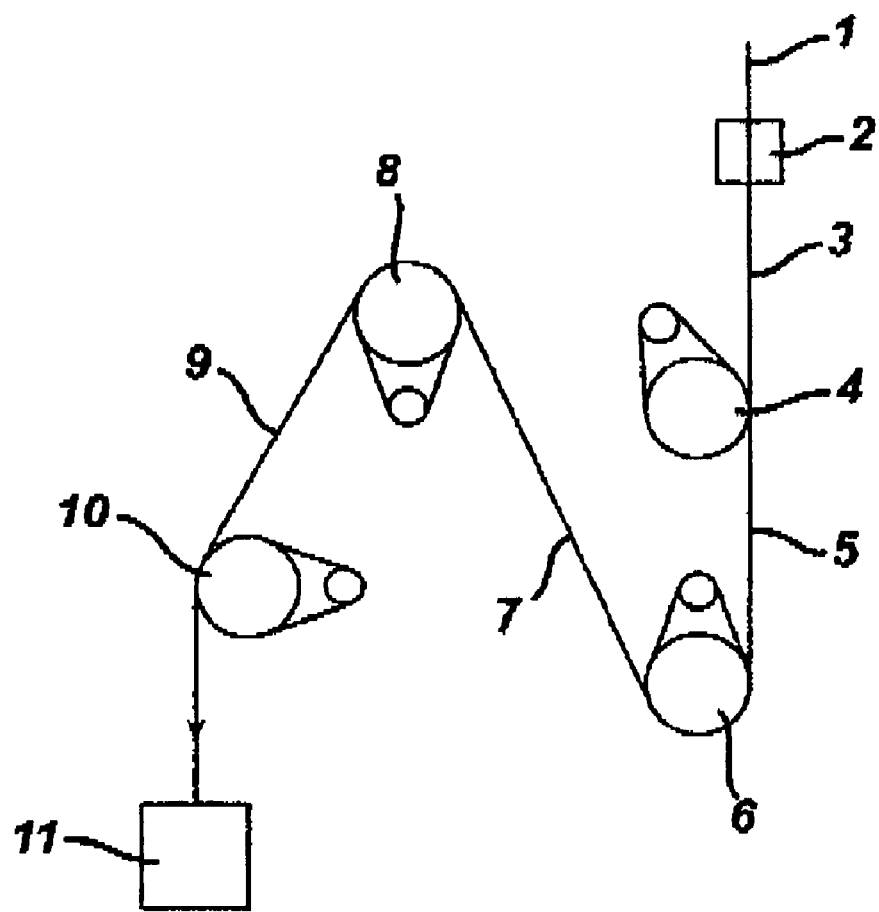
FIG. 1 is a schematic representation of the process according to the present invention.

The present invention provides a process to form a long-term bioabsorbable, biocompatible multifilament yarn from Lactide-rich copolymers. As used herein, Lactide-rich copolymers comprise from about 80% to about 98% Lactide, with the balance being polymerized monomer suitable for use in medical applications, e.g. glycolide. The process of the present invention comprises extruding and melt-spinning a Lactide-rich copolymer to form a spun multifilament yarn, pre-tensioning the spun yarn, preheating the pre-tensioned yarn, drawing and annealing the pre-tensioned, preheated yarn for a first time with a set of rolls under appropriate conditions of tension, time and temperatures, drawing and annealing the yarn for a second time with a set of rolls under appropriate conditions of tension, time and temperatures, cooling the twice-drawn yarn, and taking up the yarn. The bioabsorbable, biocompatible multifilament yarn produced by such a process exhibits synergistic properties of significantly higher tenacity, greater elongation, and greater work-to-rupture than that made by known processes. Medical devices, e.g. sutures, made from such yarns can provide long term wound support at a relatively slow absorption rate.

Preferably, the multifilament yarn made by the process of the present invention exhibits no more than two defects, e.g. broken filaments, per one kilometer. Sutures, surgical meshes, or similar surgical articles made from the multifilament yarn retain over 80% of its initial strength after three months and over 60% after 6 months, in vivo.

Bioabsorbable multifilament yarn made from Lactide-rich copolymers according to the process of the present invention exhibits a unique and synergistic combination of the properties of a tensile tenacity of at least 6 g/d, an elongation at break of at least 26%, and work-to-rupture of at least 20 g-cm/d. The resulting bioabsorbable multifilament yarn exhibits a broken filament rate of not more than five, preferably not more than two events per km (e/km). Sutures, surgical meshes or similar surgical articles made from the multifilament yarn exhibit a breaking strength retention (BSR) of at least about 80% at 90 days and at least about 60% at six months, in vivo.

The process of the present invention is depicted schematically in FIG. 1. As shown therein, a Lactide-rich copolymer is extruded and melt-spun to form multifilament spun yarn 1 according to conventional extrusion and spinning processes known to and used by those skilled in the art of making multifilament yarns for use in surgical articles such as sutures or surgical meshes. Spun yarn 1 is passed through nip roll 2 while applying a tension of at least about 5 grams to form pre-tensioned yarn 3. Pre-tensioned yarn 3 is passed through roll 4, which is heated to a temperature of from about 60° C. to about 99° C., preferably from about 75° C. to about 95° C., for a period of no more than about 6 seconds, to form pre-tensioned, preheated yarn 5. Yarn 5 then is annealed and drawn for a first time by about 4× to about 6× by passing same through roll 6, which is heated to a temperature of from about 110° C. to about 150° C., preferably from about 125 C. to about 145 C., to form drawn and annealed yarn 7. Yarn 7 then annealed and drawn for a second time by about 1.1× to about 1.3× by passing same through roll 8, which is heated to a temperature of from about 60° C. to about 150° C., preferably from about 100° C. to about 140° C., to form twice-drawn yarn 9. Yarn 9 then is passed through let-off roll 10, which preferably is at ambient temperatures, where the yarn is cooled to temperature that is lower than the second drawing temperature, before being taken up by a winding device 11 at a speed of at least about 300 m/min.

It has been found that the application of both the pre-tensioning and the preheating steps are critical in achieving the desired properties and mechanical quality of yarns according to the present invention. The pre-tension applied to the spun yarn should be at least about 5 grams, preferably from about 10 to about 60 grams. If the tension is too high or too low, excess broken filaments will occur in the drawn yarn. The preferred preheating residence time is from about 0.1 to about 6 seconds, more preferably from about 0.7 to about 2 seconds. If the yarn is heated for too long before being drawn, the yarn become brittle and broken filaments will be formed.

As shown in the examples below, which are not intended to limit the scope of the invention, the use of a heated roll in the second annealing and drawing step can significantly increase the elongation at break and the work-to-rupture of the yarn, while still maintaining a high tenacity of greater than 6.0 g/denier. The increased elongation at break and work-to-rupture is beneficial to the downstream processing of medical devices by minimizing filament breakage and defects, thus improving the yield and performance of the final products, e.g. braided sutures and surgical mesh.

The recommended ranges of process parameters for the orientation of multifilament yarns according to the present invention are given in Table 1.

EXAMPLE 1

A copolymer of 95% Lactide and 5% glycolide (weight percent) was extruded at 252° C. through a spinneret having 64 holes and wound up at 418 m/min to form a multifilament spun yarn. The spun yarn was oriented using the process parameters shown in Table 2. The residence time on the preheating roll 4 was about 1.3 seconds. Yarn properties are shown in Table 3. Yarn tenacity of greater than 6.0 g/d was maintained while the elongation and work-to-rupture were significantly increased by a proper control of the temperature of the second draw/annealing roll 8 (C-T(° C.)).

EXAMPLE 2

The same polymer utilized in Example 1 was extruded to form spun multifilament yarns under the conditions similar to example 1. The spun yarns were drawn with the same set-up as in Example 1, under a set of preferred conditions given in Table 4. The defects (i.e., broken filaments) in the drawn yarn were measured with a Fraytech counter. The yarn properties and defect rate (measured as events per kilometer) are shown in Table 5. The process yielded yarns exhibiting average tenacity of 6.5 g/d, elongation at break of 28.3%, work-to-rupture of 22.3 g-cm/d, and a defect rate of 0.33 e/km.

EXAMPLE 3

A braided size 1 suture was prepared from the yarn of example 2. The finished product had only 94 defects per 1,000 yards at final inspection. The suture had a tensile strength of about 20 pounds, and retained over 90% of the initial strength at 90 days, in vivo. In comparison, a control suture made with yarn produced by a comparative process exhibited a defect rate of 298 defects per 1,000 yards at the final inspection.

COMPARATIVE EXAMPLE 1

The same copolymer utilized in Example 1 was extruded and spun under conditions similar to Example 1, but drawn on the existing R&D Killion draw frame at a feed speed of 30 m/min under preferred conditions. The preheating residence time was about 12 seconds. The drawn yarn prepared from the preheated yarn exhibited a tenacity of 5.6 g/d, elongation at break of 23%, work to rupture of 16.7 g-cm/d, and 7.7 defects per km.

COMPARATIVE EXAMPLE 2

The same copolymer utilized in Example 1 was extruded, spun and then drawn on an existing Killion draw frame under preferred processing conditions to make a 100-denier yarn product. The feed speed was 15 ml/min and the preheating residence time was about 24 seconds. The average tenacity of the yarn thus produced was 5.8 g/d, while the elongation at break was about 24%. Excess broken filaments and defects were generated in the downstream process and detected at the final product inspection.

Yarn tensile properties of tenacity, elongation at break and work-to-rupture were determined using a Statimat Testing Machine utilizing test conditions of a gauge length of 254 mm and a strain rate of 500 mm/min were used. The work-to-rupture was determined by calculating the area under the stress strain curve, measured in the unit of g-cm/denier. The yarn defect rate was measured in events per kilometer (e/km) with an Enka Tecnica Fraytec III broken filament counter.

TABLE 1

Process Parameters for Orientation of Lactide-rich Multifilament Yarn

| Process Parameters | Unit | Inventive Process | Preferred Inventive Process | | Comparative Process |
|---|---|---|---|---|---|
| Pretension | gf | ≧5 | 10 | 60 | 0 |
| Zone 1 (OR-roll) wrap | Wraps | | 3 | 5 | 10 |
| Pre-warm Temperature | ° C. | 60–99 | 75 | 95 | 90–100 |
| Pre-warm Time | Second | 0.1–6.0 | 0.7 | 2 | 12–24 |
| Feed Roll Speed | m/min | ≧50 | 60 | 200 | 15–30 |
| 1st Draw Ratio | Times | 4–7 | 5.50 | 5.64 | 5.5 |
| 1st Draw/Annealing Temperature | ° C. | 110–150 | 125 | 145 | 138–145 |
| 1st Annealing Time | Second | 0.1–2.0 | 0.2 | 0.6 | 3–7 |
| 2nd Draw Ratio | Times | 1.05–1.30 | 1.1 | 1.2 | 1.2 |
| 2nd Draw/Annealing Temperature | ° C. | 60–150 | 100 | 140 | Ambient |
| 2nd Annealing Time | Second | 0.1–2.0 | 0.3 | 0.9 | None |
| Final Draw (Relax) Ratio | Times | 0.90–1.1 | 0.98 | 1 | None |
| Total Draw Ratio | Times | 4–9 | 6 | 7 | 6.6 |
| Winding Tension | gf | 5–50 | 8 | 30 | 10–20 |

TABLE 2

Orientation Parameters for Example 1

| Sample ID | Tension (gf) Prevention | Tension (gf) 8–10 | Tension (gf) Winding | Feed m/min | Roll 4 DR | Roll 6 DR | Roll 8 DR | Role 10 DR | TDR | Roll 10 m/min | Temperature Roll 4 (T) | Temperature Roll 6 (T) | Temperature Roll 8 (T) | Temperature Roll 10 (T) |
|---|---|---|---|---|---|---|---|---|---|---|---|---|---|---|
| A | 45 | 26.9 | 20.0 | 59.7 | 1.007 | 5.50 | 1.2 | 1.00 | 6.6 | 396.0 | 85 | 133 | 125 | amb |
| B | 33 | 21.0 | 25.0 | 59.7 | 1.007 | 5.50 | 1.2 | 1.00 | 6.6 | 396.0 | 85 | 133 | 130 | amb |
| C | 40 | 18.0 | 19.0 | 59.7 | 1.007 | 5.50 | 1.2 | 1.00 | 6.6 | 396.0 | 85 | 133 | 135 | amb |
| D | 36 | 16.0 | 23.0 | 59.7 | 1.007 | 5.50 | 1.2 | 1.00 | 6.6 | 396.0 | 85 | 133 | 140 | amb |
| E | 47 | 15.0 | 21.0 | 59.7 | 1.007 | 5.50 | 1.2 | 1.00 | 6.6 | 396.0 | 85 | 133 | 145 | amb |
| F | 38 | 12.5 | 14.0 | 59.7 | 1.007 | 5.50 | 1.2 | 1.00 | 6.6 | 396.0 | 85 | 133 | 150 | amb |
| G | 45 | 15.0 | 21.0 | 59.7 | 1.007 | 5.50 | 1.2 | 1.00 | 6.6 | 396.0 | 85 | 133 | 145 | amb |
| H | 40 | 14.5 | 2.7 | 59.7 | 1.007 | 5.50 | 1.2 | 1.00 | 6.6 | 396.0 | 85 | 133 | 145 | amb |

Notes:
DR: Draw Ratio
(T): Temperature in ° C.
TDR: Total Draw Ratio
amb: ambient

TABLE 3

Yarn Physical Properties of Example 1

| Sample ID | Yarn Denier | Tenacity Average (gpd) | Elongation Average (%) | Work-to-Rupture (g-cm/d) | Defect E/KM |
|---|---|---|---|---|---|
| A | 97.6 | 6.6 | 28.2 | 22.6 | 1.3 |
| B | 101.5 | 6.6 | 29.0 | 23.1 | 1.0 |
| C | 97.8 | 6.4 | 29.2 | 22.8 | 0.5 |
| D | 99.6 | 6.6 | 31.3 | 24.5 | 0.5 |
| E | 100.9 | 6.3 | 32.6 | 26.0 | 0.0 |
| F | 99.0 | 6.5 | 33.1 | 25.5 | 0.0 |
| G | 97.0 | 6.8 | 32.4 | 25.7 | 0.5 |
| H | 98.3 | 6.4 | 33.2 | 24.6 | 1.0 |

TABLE 4

Orientation Parameters for Example 2

| Sample ID | Feed m/min | Roll 4 DR | Roll 6 DR | Roll 8 DR | Roll 10 DR | TDR | Roll 10 m/min | Roll 4 (T) | Roll 6 (T) | Roll 8 (T) | Roll 10 (T) |
|---|---|---|---|---|---|---|---|---|---|---|---|
| A | 61.0 | 1.00 | 5.57 | 1.185 | 0.098 | 6.48 | 396.0 | 85 | 130 | 125 | amb |
| B | 61.0 | 1.00 | 5.57 | 1.185 | 0.098 | 6.48 | 396.0 | 85 | 130 | 125 | amb |
| C | 61.0 | 1.00 | 5.57 | 1.185 | 0.098 | 6.48 | 396.0 | 85 | 130 | 125 | amb |
| D | 61.0 | 1.00 | 5.57 | 1.185 | 0.098 | 6.48 | 396.0 | 85 | 130 | 125 | amb |
| E | 61.0 | 1.00 | 5.57 | 1.185 | 0.098 | 6.48 | 396.0 | 85 | 130 | 125 | amb |
| F | 61.0 | 1.00 | 5.57 | 1.185 | 0.098 | 6.48 | 396.0 | 85 | 130 | 125 | amb |
| G | 61.0 | 1.00 | 5.57 | 1.185 | 0.098 | 6.48 | 396.0 | 85 | 130 | 125 | amb |
| H | 61.0 | 1.00 | 5.57 | 1.185 | 0.098 | 6.48 | 396.0 | 85 | 130 | 125 | amb |
| I | 61.0 | 1.00 | 5.57 | 1.185 | 0.098 | 6.48 | 396.0 | 85 | 130 | 125 | amb |
| J | 61.0 | 1.00 | 5.57 | 1.185 | 0.098 | 6.48 | 396.0 | 85 | 130 | 125 | amb |
| K | 61.0 | 1.00 | 5.57 | 1.185 | 0.098 | 6.48 | 396.0 | 85 | 130 | 125 | amb |
| L | 61.0 | 1.00 | 5.57 | 1.185 | 0.098 | 6.48 | 396.0 | 85 | 130 | 125 | amb |
| M | 61.0 | 1.00 | 5.57 | 1.185 | 0.098 | 6.48 | 396.0 | 85 | 130 | 125 | amb |
| N | 61.0 | 1.00 | 5.57 | 1.185 | 0.098 | 6.48 | 396.0 | 85 | 130 | 125 | amb |
| O | 61.0 | 1.00 | 5.57 | 1.185 | 0.098 | 6.48 | 396.0 | 85 | 130 | 125 | amb |
| P | 61.0 | 1.00 | 5.57 | 1.185 | 0.098 | 6.48 | 396.0 | 85 | 130 | 125 | amb |
| Q | 61.0 | 1.00 | 5.57 | 1.185 | 0.098 | 6.48 | 396.0 | 85 | 130 | 125 | amb |

TABLE 5

Yarn Physical Properties of Example 2

| Sample ID | Yarn Denier | Tenacity (gpd) | Elongation (%) | Work-to Rupture (g-cm/d) | Defect e/km |
|---|---|---|---|---|---|
| A | 100.2 | 6.42 | 28.09 | 21.8 | |
| B | 99.7 | 6.48 | 28.68 | 22.4 | 0.03 |
| C | 100.7 | 6.78 | 28.33 | 23.4 | |
| D | 100.7 | 6.48 | 28.24 | 22.1 | 0.65 |
| E | 100.0 | 6.35 | 28.01 | 21.8 | |
| F | 100.7 | 6.66 | 28.40 | 22.9 | 0.36 |
| G | 100.7 | 6.35 | 28.34 | 22.0 | |
| H | 99.4 | 6.88 | 28.98 | 23.9 | 0.68 |
| I | 100.1 | 6.29 | 27.70 | 22.0 | |
| J | 101.3 | 6.54 | 28.32 | 22.3 | 0.34 |
| K | 101.2 | 6.14 | 27.75 | 20.9 | |
| L | 101.7 | 6.78 | 28.77 | 23.0 | 0.23 |
| M | 100.2 | 6.44 | 28.09 | 21.9 | |
| N | 101.2 | 6.59 | 29.14 | 22.5 | 0.31 |
| O | 101.0 | 6.76 | 28.47 | 23.2 | |
| P | 101.0 | 6.23 | 27.51 | 21.1 | 0.08 |
| Q | 100.5 | 6.35 | 28.63 | 21.8 | |
| Average | 100.6 | 6.51 | 28.34 | 22.33 | 0.33 |
| Std dev. | 0.62 | 0.22 | 0.45 | 0.82 | 0.24 |

We claim:

1. A process for forming bioabsorbable, biocompatible multifilament yarn from Lactide-rich copolymers, comprising:

extruding and spinning a copolymer comprising from about 80% to about 98% Lactide to form a multifilament spun yarn, applying a tension of at least about 5 grams to the spun multifilament yarn to form a pre-tensioned yarn, heating the pre-tensioned yarn at a temperature of from about 60° C. to about 99° C. for a period of not more than about 6 seconds to form a pre-tensioned, preheated yarn, annealing and drawing the pre-tensioned, preheated yarn for a first time by about 4× to about 6× at a temperature of from about 110°C. to about 150° C. for a time of about 0.1 to about 2 seconds, annealing and drawing the yarn for a second time by about 1.05× to about 1.3× at a temperature of from about 60° C. to about 150° C. for a time of about 0.1 to about 2 seconds, cooling the twice-drawn yarn; and taking-up the multifilament yarn.

2. The process of claim 1 wherein said copolymer comprises about 95 weight % Lactide and about 5 weight % Glycolide.

3. The process of claim 2 wherein the tension applied to the spun multifilament yarn to form the pre-tensioned yarn is from about 10 to about 60 grams.

4. The process of claim 3 wherein the pre-tensioned yarn is heated at a temperature of from about 75° C. to about 95° C. for a period of from about 0.1 to about 6 seconds to form the pre-tensioned pre-heated yarn.

5. The process of claim 4 wherein the pre-tensioned yarn is heated for a period of from about 0.7 to about 2 seconds to form the pre-tensioned, pre-heated yarn.

6. The process of claim 5 wherein the pre-tensioned, pre-heated yarn is annealed and drawn for the first time at a temperature of from about 125° C. to about 145° C.

7. The process of claim 6 wherein the yarn is annealed and drawn for the second time at a temperature of from about 100° C. to about 140° C.

8. The process of claim 7 wherein the yarn is annealed and drawn for the second time for about 0.3 to about 0.9 seconds.

9. A long-term bioabsorbable, biocompatible multifilament yarn, comprising a Lactide-rich copolymer, said yarn having a tenacity of at least about 6 g/d, an elongation at break of at least about 26%, and work-to-rupture of at least about 20 g-cm/d.

10. Medical devices comprising the multifilament yarn of claim 9.

* * * * *